United States Patent
Bae et al.

(10) Patent No.: US 8,394,391 B2
(45) Date of Patent: Mar. 12, 2013

(54) DRUG DELIVERY VEHICLE THAT MIMICS VIRAL PROPERTIES

(75) Inventors: You Han Bae, Salt Lake City, UT (US); Eun Seong Lee, Salt Lake City, UT (US); Dongin Kim, Salt Lake City, UT (US); Yu Seok Youn, Salt Lake City, UT (US); Kyung Taek Oh, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1397 days.

(21) Appl. No.: 11/897,979

(22) Filed: Aug. 31, 2007

(65) Prior Publication Data

US 2009/0060955 A1 Mar. 5, 2009

(51) Int. Cl.
*A61K 9/00* (2006.01)
(52) U.S. Cl. .................................................. 424/400
(58) Field of Classification Search .................. None
See application file for complete search history.

(56) References Cited

U.S. PATENT DOCUMENTS

| | | | |
|---|---|---|---|
| 5,108,921 A | 4/1992 | Low et al. | |
| 5,416,016 A | 5/1995 | Low et al. | |
| 5,688,488 A | 11/1997 | Low et al. | |
| 5,804,445 A | 9/1998 | Brasier | |
| 5,820,847 A | 10/1998 | Low et al. | |
| 7,005,426 B2 | 2/2006 | Lu et al. | |
| 7,101,567 B1 | 9/2006 | Sano et al. | |
| 7,217,410 B2 | 5/2007 | Suslick et al. | |
| 7,229,973 B2 | 6/2007 | Bae et al. | |
| 7,316,811 B2 * | 1/2008 | Zhao et al. | 424/78.27 |
| 2003/0125302 A1 | 7/2003 | Lu et al. | |
| 2004/0258762 A1 | 12/2004 | Boppart et al. | |
| 2005/0002948 A1 * | 1/2005 | Ryall | 424/184.1 |
| 2005/0118252 A1 | 6/2005 | Bae et al. | |
| 2005/0118718 A1 * | 6/2005 | Bae et al. | 435/458 |
| 2007/0154396 A1 | 7/2007 | Wang et al. | |
| 2007/0154398 A1 | 7/2007 | Wang et al. | |

OTHER PUBLICATIONS

Kim et al. (Macromolecular Bioscience. 2005; 5: 1118-1124).*
Takakura et al. (Pharmaceutical Research. 1996; 13 (6): 820-831).*

* cited by examiner

*Primary Examiner* — Shanon A Foley
(74) *Attorney, Agent, or Firm* — Clayton, Howarth & Cannon, P.C.

(57) ABSTRACT

A drug delivery vehicle for targeted delivery of a drug mimics viral properties of size, capsid-like protein capsule, cell-specific entry, toxin release, destruction of infected cells, and migration to neighboring cells. This vehicle, termed a virogel, contains a hydrophobic polymeric core, a hydrophilic inner shell, a hydrophilic outer shell, and a ligand. An illustrative drug-loaded virogel includes poly(L-histidine-co-phenylalanine) as the core, doxorubicin loaded in the core, polyethylene glycol as the inner shell, bovine serum albumin as the outer shell, and folic acid as the ligand.

9 Claims, 6 Drawing Sheets

DRUG DELIVERY VEHICLE THAT MIMICS VIRAL PROPERTIES

STATEMENT REGARDING FEDERALLY SPONSORED RESEARCH OR DEVELOPMENT

This invention was made with government support under grant no. CA122356 and grant no. CA101850 from the National Institutes of Health. The government has certain rights in the invention.

CROSS-REFERENCE TO RELATED APPLICATIONS

Not applicable.

BACKGROUND OF THE INVENTION

This invention relates to drug delivery vehicles. More particularly, this invention relates to a drug delivery vehicle that mimics viral properties, such as size, possession of a capsid-like protein capsule, cell-specific entry, toxin release, destruction of infected cells, and migration to neighboring cells.

Viruses infect specific cells within host organisms, replicate, destroy the cells, and spread from cell to cell in infectious cycles, causing diseases. S. S. Whitehead et al., Prospects for a dengue virus vaccine, 5 Nat. Rev. Microbiol. 518-528 (2007). These viral properties have inspired synthetic designs of various delivery vehicles, particularly for toxic anticancer agents that exhibit numerous side effects. Y. Geng et al., Shape effects of filaments versus spherical particles in flow and drug delivery, 2 Nat. Nanotechnol. 249-255 (2007); Z. Huang et al., Thiocholesterol-based lipids for ordered assembly of bioresponsive gene carriers, 11 Mol. Ther. 409-417 (2005); D. Putnam, Polymers for gene delivery across length scales, 5 Nat. Mater. 439-451 (2006). Drug delivery vehicles may mimic certain aspects of viruses, such as size, Y. Sasaki, Cerasome as an infusible and cell-friendly gene carrier: synthesis of cerasome-forming lipids and transfection using cerasome, 1 Nat. Protocols 1227-1234 (2006), and surface properties, Z. Huang et al., supra, to improve cell entry and residence within the body before being cleared.

While prior drug delivery vehicles are known and are generally suitable for their limited purposes, they possess certain inherent deficiencies that detract from their overall utility in drug delivery.

In view of the foregoing, it will be appreciated that providing a drug delivery vehicle that mimics viral size, capsid-like protein capsule, cell-specific entry, toxin release, destruction of infected cells, and migration to neighboring cells would be a significant advancement in the art.

BRIEF SUMMARY OF THE INVENTION

An illustrative embodiment of the present invention comprises a drug delivery vehicle for targeted delivery of a drug to a selected site, the drug delivery vehicle comprising a hydrophobic polymeric core configured for receiving the drug, a hydrophilic inner shell coupled to the core, a hydrophilic outer shell coupled to the inner shell, and a ligand coupled to the outer shell. An illustrative core comprises poly(L-histidine-co-phenylalanine), such as wherein the poly(L-histidine-co-phenylalanine) comprises blocks each containing about 32 histidine residues and about 6 phenylalanine residues. An illustrative hydrophilic inner shell comprises polyethylene glycol. An illustrative hydrophilic outer shell comprises a protein, such as bovine serum albumin (BSA). Each bovine serum albumin molecule may be coupled to more than one polyethylene glycol molecule. An illustrative ligand according to the present invention comprises a vitamin, a hormone, an interleukin, a growth factor, a neurotransmitter, a viral surface component, an antibody, an antigen-binding protein, a carbohydrate, or a lectin. An example of such a ligand is folic acid.

Another illustrative embodiment of the invention comprises a composition for targeted delivery of a drug to a selected site, the composition comprising a hydrophobic polymeric core, the drug disposed in the core, a hydrophilic inner shell coupled to the core, a hydrophilic outer shell coupled to the inner shell, and a ligand coupled to the outer shell.

Still another illustrative embodiment of the present invention comprises a method of delivering a drug to a target cell bearing a ligand-binding agent. The method comprises administering a drug-loaded composition to an individual, wherein the composition comprises a hydrophobic polymeric core, the drug disposed in the core, a hydrophilic inner shell coupled to the core, a hydrophilic outer shell coupled to the inner shell, and a ligand coupled to the outer shell, wherein the drug-loaded composition circulates in the individual until it contacts the target cell and the ligand portion of the drug-loaded composition binds to the ligand-binding agent on the target cell, thereby delivering the drug to the target cell. With an appropriately selected combination of ligand and target cell bearing the ligand-binding agent, the composition enters the cell by receptor-mediated endocytosis, thus delivering the drug inside the target cell.

Yet another illustrative embodiment of the invention comprises a method of treating cancer, the method comprising administering a drug-loaded composition to an individual in need thereof, wherein the composition comprises a hydrophobic polymeric core comprising poly(L-histidine-co-phenylalanine), an anticancer drug disposed in the core, a hydrophilic inner shell comprising polyethylene glycol coupled to the core, a hydrophilic outer shell comprising bovine serum albumin coupled to the inner shell, and a folic acid ligand coupled to the outer shell, wherein the composition circulates in the individual until it contacts cancer cells bearing a folate receptor and the folic acid ligand of the composition binds to the folate receptor on the cancer cells, triggering receptor-mediated endocytosis, thereby delivering the anticancer drug into the cancer cells.

BRIEF DESCRIPTION OF THE SEVERAL VIEWS OF THE DRAWINGS

In FIG. 3A, pH was adjusted between pH 7.4 (A) and pH 6.8 (B), and in FIG. 3B, pH was adjusted between pH 7.4 (A) and pH 6.4 (C).

DETAILED DESCRIPTION

Before the present drug delivery vehicle and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a composition containing "a drug" includes a mixture of two or more drugs, reference to "a protein" includes reference to one or more of such proteins, and reference to "a ligand" includes reference to two or more of such ligands.

Unless defined otherwise, all technical and scientific terms used herein have the same meanings as commonly understood by one of ordinary skill in the art to which this invention belongs.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of." As used herein, "consisting of" and grammatical equivalents thereof exclude any element, step, or ingredient not specified in the claim. As used herein, "consisting essentially of" and grammatical equivalents thereof limit the scope of a claim to the specified materials or steps and those that do not materially affect the basic and novel characteristic or characteristics of the claimed invention.

As used herein, "protein" means peptides of any length and includes oligopeptides, polypeptides, and proteins. The terms "protein," "polypeptide," and "oligopeptide" are to be construed without any particular intended size limitation, unless a particular size is otherwise stated.

As used herein, "administering" and similar terms mean delivering the composition to the individual being treated such that the composition is capable of being circulated systemically to the parts of the body where the drug can carry out its pharmacological effect on its intended cellular target. Thus, the composition is typically administered to the individual by systemic administration, typically by subcutaneous, intramuscular, or intravenous administration, or intraperitoneal administration. However, other means of administration, such as injection directly into a tumor, are also within the scope of the invention. Injectables for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances, such as wetting or emulsifying agents, buffers, and the like can be added.

As used herein, "ligand" means any molecule that binds to another, usually through specific, reversible interactions of multiple weak, non-covalent bonds. Examples of ligands include vitamins, hormones, interleukins, growth factors, neurotransmitters, and viral surface components that bind to receptors on the surfaces of cells; antibodies, antigen-binding proteins, carbohydrates, lectins, and the like. Still another example is the HIV gp120 envelope glycoprotein, which binds with specific receptors—the CD4 glycoprotein and members of the chemokine receptor family. The CD4 glycoprotein is expressed on the surface of T lymphocytes, monocytes, dendritic cells, and brain microglia, the main target cells for primate immunodeficiency viruses in vivo. Another example of a ligand is interleukin-2 (IL-2), which binds to the high-affinity IL-2 receptors found on a subset of activated T-lymphocytes thought to be the main or sole site of HIV replication.

As used herein, "antibody" means an immunoglobulin molecule that interacts with the antigen that induced its synthesis in lymphoid tissue or with antigens closely related to it. Included within this definition of antibody all antibody types, e.g., IgG, IgA, IgM, etc.; IgG subclasses, e.g., IgG1, IgG2, etc.; F(ab) fragments; F(ab')$_2$ fragments; F(ab') fragments; light chain dimers; and the like. This definition also includes antibodies that react with low and high affinity with an antigen.

As used herein, "carbohydrate" means carbohydrate monomers, oligomers, and polymers. There is no particular intended size limitation with respect to carbohydrate oligomers or polymers unless a particular size is otherwise stated.

As used herein, "lectin" means a class of proteins of non-immunological origin that binds carbohydrates. The scope of lectins that can be used according to the present invention is limited only by functionality, i.e., binding to carbohydrates. Segments or portions of lectins are also to be considered within the scope of the term "lectin" provided that such segments or portions retain the carbohydrate-binding function. Representative lectins that can be used according to the present invention include the following: abrin or jequirity bean (*Abrus precatorius*), asparagus pea or lotus or winged pea (*Tetragonolobus purpureas*), avocado (*Persea americana*), bitter pear melon (*Momordica charantia*), broad bean (*Vicia faba*), camels foot tree (*Bauhinia purpurea*), castor bean (*Ricinus communis*), chick pea (*Cicer arietinum*), Mozambique cobra (*Naja mocambique mocambique*), Thailand cobra (*Naja naja laculbia*), concanavalin A or jack bean (*Canavalia ersiformis*), Israel coral tree (*Erythina oxaliodendron*), daffodil (*Narcissus pseudonarcissus*), eel (*Anguilla anguilla*), elderberry (*Sambucus nigra*), furze or gorse (*Ulex

*europaeus*), green marine algae (*Cocleum fragile*), hairy vetch (*Vicia villosa*), horse gram (*Dolichos biflorus*), horseshoe crab or limulin (*Limulus polyphemus*), jacalin (*Artocarpus integrifolia*), Japanese wisteria (*Wisteria floribunda*), jimson weed or thorn apple (*Datura stramonium*), Scotch laburnum (*Laburnum alpinum*), lentil (*Lens culinaris*), lima bean (*Phaseolus limensis*), European mistletoe or viscumin (*Viscum album*), mung bean (*Vigna radiata*), mushroom (*Agaricus bisporus*), Osage orange (*Maclura pomifera*), pagoda tree (*Sophora japonica*), pea (*Pisum sativum*), peanut (*Arachis hypogaea*), pokeweed (*Phytolacca americana*), potato (*Solanum tuberosum*), red kidney bean (*Phaseolus vulgaris*), red marine algae (*Plifola plumosa*), Roman snail (*Helix porrata*), scarlet runner bean (*Phaseolus coccineus*), Scotch broom (*Cytisus scoparius*), Siberian pea tree (*Caragana arborescens*), snail-edible (*Helix pomatia*), snail-garden (*Helix aspersa*), snowdrop (*Galanthus nivalis*), soybean (*Glycine max*), spindle tree (*Euonymus europaeus*), sweet pea (*Lathyrus odoratus*), tomato (*Lycopersicon esculentum*), wheat germ (*Triticum vulgaris*), winged bean (*Psophoramus beliagonolobus*). Additional lectins include tora-mame lectin (from *Phaeolus vulgaris*), phytohemagglutinin (PHA), wheat germ agglutinin, achatinin H, and *Vicia villosa* lectin. Still additional lectins include lectins that bind to T lymphocytes, including mistletoe lectin, *Phaseolus vulgaris* leucoagglutinin, and lectins from *Bandeiraea simplicifolia* BS-I, *Bauhinia purpurea, Glycine max, Lycopersicon esculentum, Triticum vulgaris, Canavalia ensiformis, Lens culinaris, Phaseolus coccineus*, and *Wisteria floribunda*. Further additional lectins include lectins that bind to sulfated carbohydrates, such as L-selectin and human galectin 1. Another group of lectins include the B subunits of Shiga and Shiga-like toxins (SLTs), such as the B chains of Shiga toxin, SLT-I, SLT-II, SLT-IIv, and SLT-2e. Still other lectins include mannose binding proteins and maltose binding protein.

As used herein, "drug" means a substance used in the diagnosis, treatment, or prevention of a disease or as a component of a medication. In one embodiment of the present invention, the drug may be hydrophobic. Hydrophobic drugs are compounds with little or no water solubility. Intrinsic water solubilities (i.e., water solubility of the unionized form) for hydrophobic drugs are less than about 1% by weight, and typically less than about 0.1% or 0.01% by weight.

Suitable drugs are not limited by therapeutic category, and can be, for example, analgesics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leucotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

Specific, non-limiting examples of suitable hydrophobic drugs include acutretin, albendazole, albuterol, aminogluthemide, amiodarone, amlodipine, amphetamine, amphotericin B, atorvastatin, atovaquone, azithromycin, baclofen, beclomethsone, benezepril, benzonatate, betamethasone, bicalutanide, budesonide, bupropion, busulphan, butenafine, calcifediol, calciprotiene, calcitriol, camptothecan, candesartan, capsaicin, carbamezepine, carotenes, celecoxib, cerivistatin, cetrizine, chlorpheniramine, cholecalciferol, cilostazol, cimetidine, cinnarizine, ciprofloxacin, cisapride, clarithromycin, clemastine, clomiphene, clomipramine, clopidrogel, codeine, coenzyme Q10, cyclobenzaprine, cyclosporine, danazol, dantrolene, dexchlopheniramine, diclofenac, dicoumarol, digoxin, dihydro epiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, flucanazole, flurbiprofen, fluvastatin, fosphenytion, frovatriptan, furazolidone, gabapentin, gemfibrozil, glibenclamide, glipizide, glyburide, glymepride, griseofulvin, halofantrine, ibuprofen, irbesartan, irinotecan, isosorbide dinitrate isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol acetate, methadone, methoxsalen, metronidazole, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osteradiol, oxaprozin, paclitaxel, paricalcitol, paroxetine, pentazocine, pioglitazone, pizofetin, pravastatin, prednisolone, probucol, progesterone, pseudo-ephedrine, pyridostigmine, rabeprazole, raloxifene, refocoxib, repaglinide, rifabutine, rifapentine, rimexolone, ritanovir, rizatriptan, rosigiltazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terzosin, tetrahydrocannabinol, tiagabine, ticlidopine, tirofibran, tizanidine, topiramate, topotecan, toremifene, tramadol, tretinoin, troglitazone, trovafloxacin, ubidecarenone, valsartan, venlafaxine, vertoporfin, vigabatrin, vitamin A, vitamin D, vitamin E, vitamin K, zafirlukast, zileuton, zolmitriptan, zolpidem, and zopiclone. Of course, salts, isomers and derivatives of the above-listed hydrophobic active ingredients may also be used, as well as mixtures thereof.

Illustrative anticancer drugs include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene hcl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflomithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride. Flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmetteguerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

The present invention relates to a synthetic nano-sized polymer vehicle exhibiting viral properties more significant than any known delivery systems. C. J. H. Porter, N. L. Trevaskis & W. N. Charman, Lipids and lipid-based formulations: optimizing the oral delivery of lipophilic drugs, 6 Nat. Rev. Drug Discov. 231-248 (2007). Specifically, embodiments of this particle design comprise a capsid-like protein capsule, cell-specific entry, toxin release, destruction of infected cells, and migration to neighboring cells. A. Tkachenko et al., Assembly and characterization of biomolecule-gold nanoparticle conjugates and their use in intracellular imaging, 303 Methods Mol. Biol. 85-99 (2005); D. W. Kuykendall & S. C. Zimmerman, Nanoparticles: a very versatile nanocapsule, 2 Nat. Nanotechnol. 201-202 (2007). Remarkably, these traits are shown over repeated cycles in cultures of drug-resistant tumor cells. M. Tijerina et al., Chronic exposure of human ovarian carcinoma cells to free or HPMA copolymer-bound mesochlorin e6 does not induce P-glycoprotein-mediated multidrug resistance, 21 Biomaterials 2203-2210 (2000); G. Szakacs et al., Targeting multidrug resistance in cancer, 5 Nat. Rev. Drug Discov. 219-234 (2006). This virus-like infectious nanogel (hereinafter termed "virogel") may be used for treating several major disease classes, such as tumors.

FIG. 1 shows a schematic representation of an illustrative embodiment of a virogel according to the present invention. The virogel 10 comprises a hydrophobic polymer core 12, an inner layer 14 of hydrophilic shell (or "inner shell"), and an outer layer 16 of hydrophilic shell (or "outer shell"). In an illustrative embodiment, the hydrophobic polymer core 12 may comprise poly(L-histidine-co-phenylalanine), such as poly($His_{32}$-co-$Phe_6$), which contains 32 histidine ("His") monomers and 6 phenylalanine ("Phe") monomers in each block. The hydrophobic polymer core 12 may be loaded with a drug that is to be delivered. For example, a model anticancer drug, doxorubicin ("DOX"), may be loaded in the hydrophobic polymer core 12. The inner shell 14 may comprise a hydrophilic polymer. In an illustrative embodiment of the present invention, the inner shell 14 may comprise poly(ethylene glycol) ("PEG"). For example, PEG having an average molecular weight of about 2000 Da may be used to form the inner shell 14. One end of the PEG is linked, typically by a covalent bond, to the core polymer, and the other end of the PEG is linked, typically by a covalent bond, to the outer shell 16. The outer shell 16 may be formed of a hydrophilic protein. In one illustrative embodiment of the present invention, the outer shell 16 is comprised of bovine serum albumin ("BSA"), which is linked to multiple PEG molecules, as illustrated in FIG. 1. The outer shell 16 may also be conjugated with ligands 18 for specific recognition of receptors or other ligand-binding agents borne on the surface of selected cells. In one illustrative embodiment, such ligands 18 may comprise folic acid, which is specifically recognized by folate receptors, which are over-expressed on the surface of many tumors. R. Duncan. Polymer conjugates as anticancer nanomedicines, 6 Nat. Rev. Cancer 688-701 (2006).

As mentioned above, the virogels are synthesized with ligands selected to target cells of interest. For example, folic acid may be used to target tumors, since folate receptors are over-expressed on the surface of many tumors. By way of further example, HIV gp120 glycoprotein may be used to target CD4 glycoprotein, which is expressed on the surface of T lymphocytes. Virogels are loaded with a selected drug, or a combination of drugs, for treating a selected disease or condition. For example, anticancer drugs may be selected for treating cancer. The drug-loaded virogels may then be administered to an individual in need of treatment. After administration, the virogels may circulate in the body until they contact cells of interest. Once contact is made, the ligand is bound by its corresponding receptor or other ligand-binding agent. This event triggers receptor-mediated endocytosis, such that the virogels are endocytosed into the cell. Experimental results described herein indicate that the virogels are released from endosomes into the cytosol, probably due to the physical expansion of the virogels at endosomal pH. The drug also is released from the virogels at endosomal pH. Once in the cytosol, the drug may diffuse into the nucleus.

The following examples are intended to illustrate certain aspects of the present invention. These examples are not to be considered as limitations on the invention, since the scope of the invention will be defined by the claims and equivalents thereof.

Example 1

A poly($His_{32}$-co-$Phe_6$) copolymer comprising H is (32 repeating units) and Phe (6 repeating units) was synthesized by ring-opening co-polymerization of protected H is N-carboxyanhydride (NCA) and Phe NCA. The copolymer block was then coupled with PEG ($M_w \approx 2000$) via an amide bond, as described in G. M. Kim, Y. H. Bae & W. H. Jo, pH-induced micelle formation of poly(histidine-co-phenylalanine)-block-poly(ethylene glycol) in aqueous media, 5 Macromol. Biosci. 1118-1124 (2005). Next, the protecting benzyl group of H is NCA was deprotected. Id. The yields of the final copolymer (poly($His_{32}$-co-$Phe_6$)-b-PEG) ranged from about 70 wt % to about 85 wt %. Modification of the open end of PEG with a succinyl ester was performed in dimethylformamide (50 ml, DMF; Sigma-Aldrich, St. Louis, Mo.) with N,N'-disuccinimidyl carbonate (2.5 mol; Sigma-Aldrich) and poly($His_{32}$-co-$Phe_6$)-b-PEG with hydrochloride salt (1 mol), A. Patchomik et al., Poly-L-histidine, 79 J. Am. Chem. Soc. 5227-5230 (1957), and was purified by recrystallization using dimethyl formamide (DMF; Sigma-Aldrich) and excess diethyl ether (Sigma-Aldrich). G. M. Kim, Y. H. Bae & W. H. Jo, supra. The structure of the core and inner PEG shell was constructed by an oil-in-water emulsion method, S. V. Vinogradov et al., Nanogels for oligonucleotide deliver to the brain, 15 Bioconjug. Chem. 50-60 (2004).

The poly(His$_{32}$-co-Phe$_6$)-b-PEG-succinyl ester core and inner shell (4 mg) was dissolved in dichloromethane (0.1 ml; Sigma-Aldrich) with and without triethylamine-treated DOX (1 mg; DOX.HCl, Sigma-Aldrich), E. S. Lee, K. Na & Y. H. Bae, Polymeric micelle for tumor pH and folate-mediated targeting, 91 J. Control. Release 103-113 (2003); E. S. Lee, K. Na & Y. H. Bae, Super pH-sensitive multifunctional polymeric micelle, 5 Nano Lett. 325-329 (2005), and BSA (1 mg; Sigma-Aldrich) was dissolved in 0.9 ml phosphate buffered saline (PBS; pH 7.4, 20 mM). The two solutions were vigorously stirred at 10,000 rpm for 10 min, followed by gentle stirring at 1,000 rpm for 20 min, which resulted in attachment of the BSA to the free ends of the PEG of the inner shell. Residual dichloromethane was evaporated at 30° C. for 12 hours. After ultracentrifugation at 25,000 rpm, which precipitated the virogels, a supernatant was extracted and tested using a BCA protein assay kit (Pierce, Milwaukee, Wis.) to measure the content of the unreacted BSA. The results showed that 90±5 wt % (n=3) of feed BSA reacted with the PEG-succinyl ester portion of the core and inner shell. This indicates that the BSA content was about 180 µg per 1 mg of virogel. The content of DOX loaded in the virogels was determined using a UV/Visible spectrophotometer, as described in E. S. Lee, K. Na & Y. H. Bae, Polymeric micelle for tumor pH and folate-mediated targeting, 91 J. Control. Release 103-113 (2003). The results confirmed that 85±5 wt % of the DOX feed was incorporated into virogels.

Example 2

Fluorescein isocyanate (FITC; 0.2 mg; Sigma-Aldrich) or folate-succinyl ester (0.2 mg) was coupled to virogels (4 mg), prepared according to the procedure of Example 1, at room temperature for 3 hours. E. S. Lee, K. Na & Y. H. Bae, Super pH-sensitive multifunctional polymeric micelle, 5 Nano Lett. 325-329 (2005); E. S. Lee, K. Na & Y. H. Bae, Doxorubicin loaded pH-sensitive polymeric micelles for reversal of resistant MCF-7 tumor, 103 J. Control. Release 405-418 (2005). The fluorescein-labeled virogels were prepared to permit confocal imaging of virogels within cells. Approximately 85±5 wt % of feed FITC and 80±4 wt % of folate reacted with the virogels, determined by residual amounts of FITC or folate in the supernatants obtained by ultracentrifugation of the virogel solution at 25,000 rpm. Concentrations were measured by high performance liquid chromatography (HPLC). Unreacted reagents were removed by dialysis.

Example 3

Figure 1:
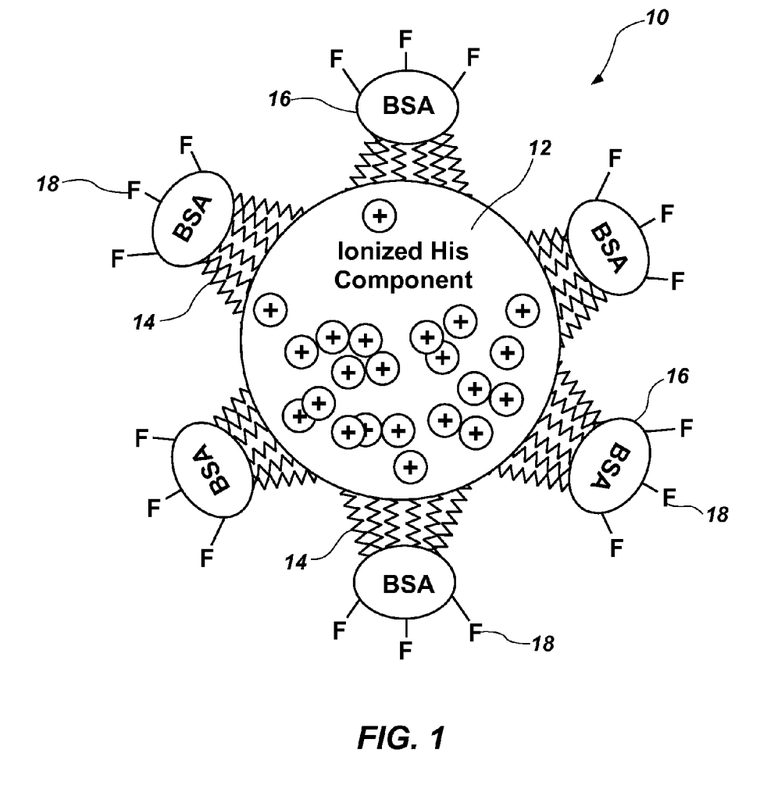
FIG. 1 shows a schematic representation of an illustrative embodiment of a virogel drug delivery vehicle according to the present invention.
Figure 2:
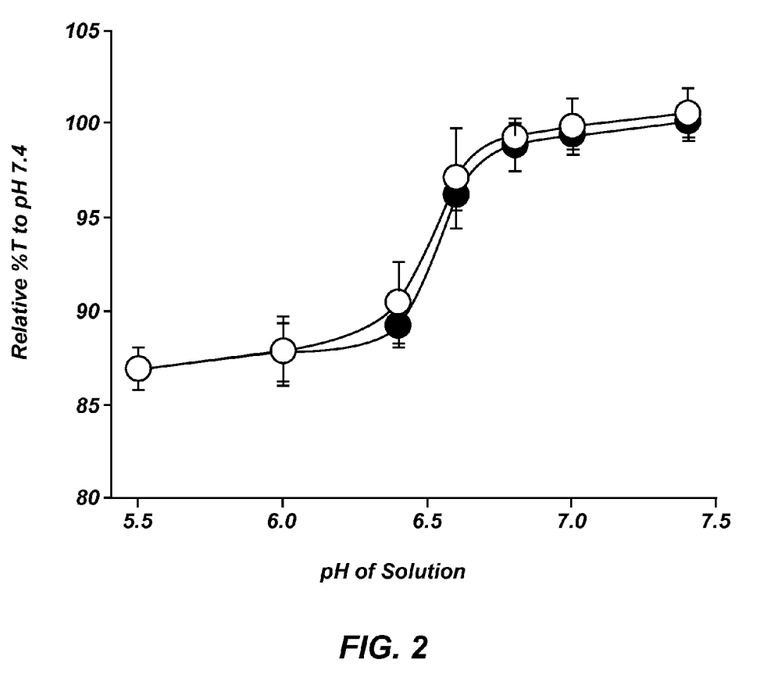
FIG. 2 shows relative % transmittance (% T) of a virogel-containing solution with changing pH, where open circles indicate measurements taken with gradual change from pH 7.4 to pH 5.5, and closed circles indicate measurements taken with gradual change from pH 5.5 to pH 7.4.

Virogel sensitivity to pH was assessed using optical transmittance of an aqueous virogel solution. Transmittance was measured with a UV/Visible spectrophotometer (wavelength of 500 nm). Before testing, the pH of the virogel solution (0.01 wt, ionic strength: 0.15) was reversibly changed between pH 7.4 and pH 5.5 and was stabilized at 37° C. for 1 hour at each pH. Relative transmittance of the virogel solution was measured at each selected pH with respect to transmittance at pH 7.4. As shown in FIG. 2, the % transmittance (% T) dropped sharply over a narrow pH range of about 6.6-6.4 upon reduction of the pH from 7.4 to 5.5. When the pH was increased again, the % T recovered with a small hysteresis. The observed % T change is attributed to the dynamic dimensional changes of virogels with pH, as shown in Example 4.

Example 4

Figure 3A:
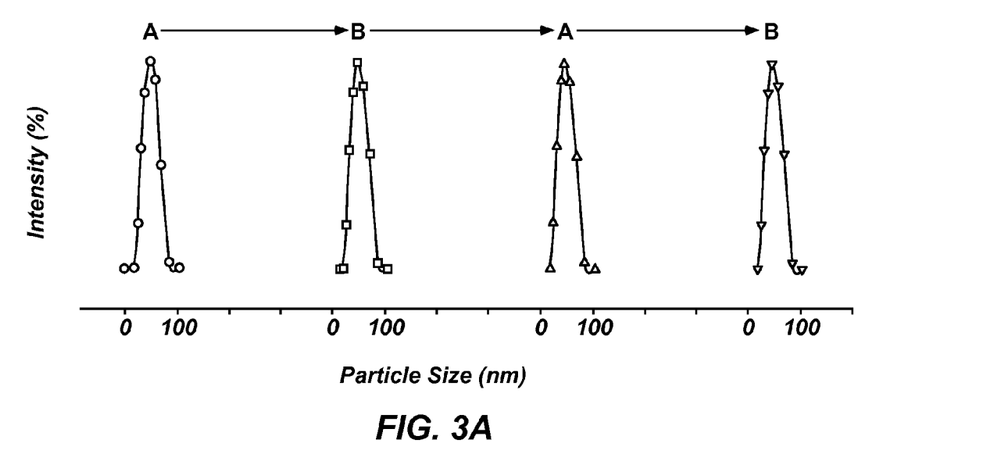
FIGS. 3A and 3B show virogel size changes as determined by dynamic light scattering as a function of pH change.
Figure 3B:
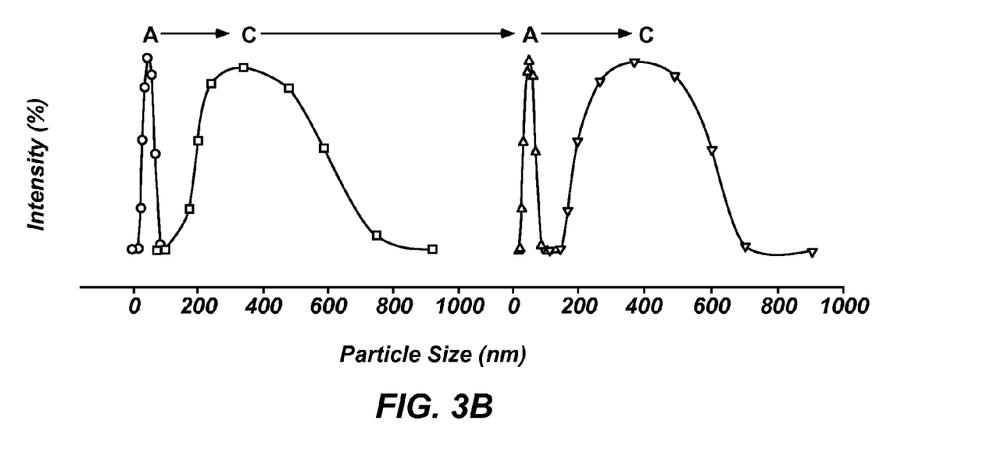

Dynamic light scattering (Malvern Instrument) was used to determine the particle size of the virogels as a function of pH. Solutions containing virogels were adjusted from pH 7.4 (A) to pH 6.8 (B) to pH 7.4 (A) to pH 6.8 (B), as shown in FIG. 3A, or from pH 7.4 (A) to pH 6.4 (C) to pH 7.4 (A) to pH 6.4 (C), as shown in FIG. 3B. Virogels were equilibrated at each pH for 1 hour before measurements were taken. As a control, the particle size of BSA was also measured as a function of pH. BSA showed no significant difference in particle size with changes in pH.

The pK$_b$ of L-histidine of the core is near 6.4, G. M. Kim, Y. H. Bae & W. H. Jo, supra, as measured by an acid-base titration method. At high pH, the virogel core is rigid. However, the core swells spontaneously when the polymer H is residues are protonated at lower pH. G. M. Kim, Y. H. Bae & W. H. Jo, supra; E. S. Lee et al., Poly(L-histidine)-PEG block copolymer micelles and pH-induced destabilization, 90 J. Control. Release 363-374 (2003). The typical cytosolic pH within cells ranges from pH 7.2 to pH 6.8. M. A. Schwartz et al., Effect of cell spreading on cytoplasmic pH in normal and transformed fibroblasts, 86 Proc. Nat'l Acad. Sci. USA 4525-4529 (1989). Light scattering data show that virogels have a particle size of about 55 nm at pH 7.4, slightly increasing to about 64 nm at pH 6.8. When the pH cycled between pH 7.4 and pH 6.8, virogels swelled and shrank reversibly, as shown in FIG. 3A. Additionally, virogel particle size changes upon repeated cycling between pH 7.4 and pH 6.4 were also reversible, as shown in FIG. 3B.

Illustrative embodiments of virogels are designed to interact with target cells via folate-FR coupling, triggering uptake, R. Duncan, supra; S. Sabharanjak & S. Major, Folate receptor endocytosis and trafficking, 56 Adv. Drug Deliv. Rev. 1099-1109 (2004), and subsequent localization within early endosomes. Endosomes naturally acidify their contents by activating endogenous proton pumps, dropping compartment pH. D. Schmaljohann, Thermo- and pH-responsive polymers in drug delivery, 58 Adv. Drug Deliver. Rev. 1655-1670 (2006). When the virogels are exposed to early endosomal pH of 6.4, Id., their sizes grow abruptly, reaching 355 nm. Apparently, virogel structure is maintained during this size change by virtue of the capsid-like BSA shell holding multiple interior core block copolymers by PEG linkages, preventing them from dissociating even after ionization of the core H is component at lower pH. Flexible tethering of the BSA corona to the pH-sensitive core by the PEG units accommodates a large extent of expansion without particle disassembly. Hydrophobic interaction among core polymer Phe components is believed to help avoid dissociation.

Example 5

Human ovarian carcinoma A2780 cells (ATCC, Manassas, Va.) were maintained in RPMI-1640/PBS medium (Gibco, Uxbridge, UK) with 0.5 M PBS, 2 mM L-glutamine (Sigma-Aldrich), 5% penicillin-streptomycin (Gibco), and 10% fetal bovine serum (Gibco) in a humidified incubator at 37° C. and 5% CO$_2$ atmosphere. Before testing, cultured cells (1×10$^6$ cells/ml) monolayers were harvested with 0.25% (w/v) trypsin-0.03% (w/v) EDTA solution (Gibco). Cells were incubated with FITC-labeled virogels (10 µg/ml, pH 7.4), prepared according to the procedure of Example 2, and confocal slice images were obtained at 60, 80, and 90 minutes. Fluorescence intensity within cells grown on Lab-Tek II chamber slides or slide glass fragments were examined with a Leica TCS NT confocal microscope using appropriate optical filters for the FITC probe. All confocal images were slice images, E. S. Lee, K. Na & Y. H. Bae, Polymeric micelle for tumor pH and folate-mediated targeting, 91 J. Control. Release 103-113 (2003); E. S. Lee, K. Na & Y. H. Bae, Super pH-sensitive multifunctional polymeric micelle, 5 Nano Lett. 325-329 (2005), to distinguish virogels internalized from those adherent to the outside cellular membrane.

Figure 4:
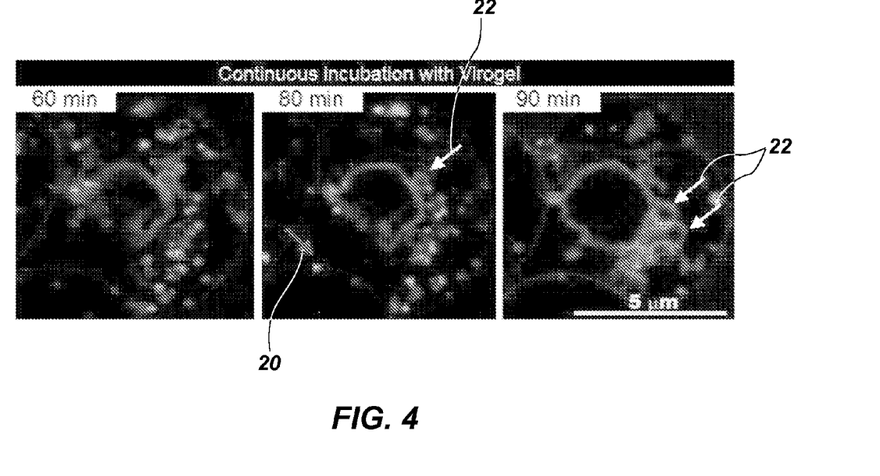
FIG. 4 shows confocal slice images of virogels in a living ovarian A2780 cell at 60, 80, and 90 minutes of incubation.

FIG. 4 shows the co-existence of unswollen and swollen virogels in live human ovarian carcinoma A2780 cells, traced by a series of confocal slice images taken for a single cell at 10-minute intervals. The arrow 20 indicates an unswollen virogel, and arrows 22 indicate swollen virogels. Swollen virogels appear after 60 min as hollow spheres, due to the surface localized FITC on the BSA shell. The dimensions of the virogels in both states coincide with particle sizes measured by light scattering (FIG. 3B).

Example 6

DOX-loaded virogels prepared according to the procedures of Examples 1 and 2 were placed in PBS pH 7.4 solution (1 ml, ionic strength: 0.15) in a dialysis membrane tube (Spectra/Por MWCO 5000). The tubes were then immersed in a vial containing fresh PBS (20 ml) at pH 7.4, pH 6.8, or pH 6.4 for one hour at 37° C. with shaking at 100 rev/min. DOX concentrations were determined with a UV/Visible spectrophotometer. E. S. Lee, K. Na & Y. H. Bae, Polymeric micelle for tumor pH and folate-mediated targeting, 91 J. Control. Release 103-113 (2003).

Figure 5:
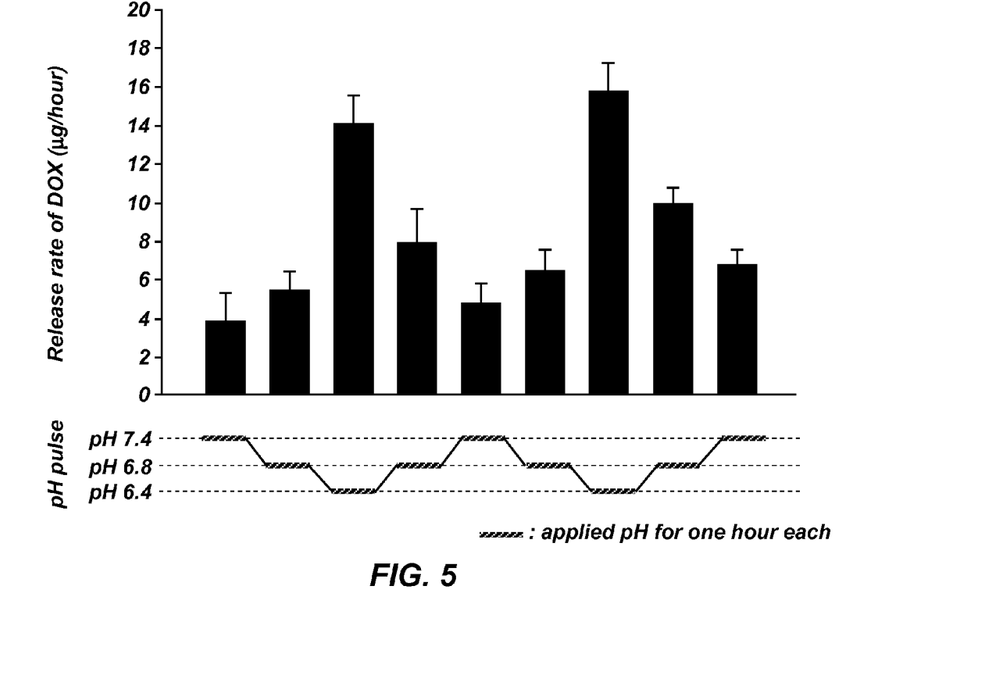
FIG. 5 shows release rates of doxorubicin (DOX) from DOX-loaded virogels at selected hydrogen ion concentrations.

FIG. 5 shows pH-dependent DOX release rate. For the initial loading of DOX of 150 µg per mg of virogel, a DOX release rate for the first hour at pH 7.4 was about 3.8 µg/hour, slightly increased to 5.4 µg/hour at pH 6.8 for the second hour, and sharply increased to about 14 µg/hour at pH 6.4. Upon increasing pH, the rate was 8.0 µg/hour at pH 6.8 and 4.6 µg/hour at pH 7.4. The release rate hysteresis is likely due to the short non-equilibrium time frame (one hour interval) used for changing pH and sampling. A similar pattern was observed in the second pH cycle, closely reproducing the initial release rates at each pH.

Due to the known proton buffering effect, A. de Fougerolles et al., Interfering with disease: a progress report on siRNA-based therapeutics, 6 Nat. Rev. Drug Discov. 443-453 (2007); D. Putnam et al., Polymer based gene delivery with low cytotoxicity by a unique balance of side-chain termini, 98 Proc. Nat'l Acad. Sci. USA 1200-1205 (2001), of polyHis or poly(His$_{32}$-co-Phe$_6$) (L-histidine is the most effective pH-buffering agent in a physiological system, G. M. Kim, Y. H. Bae & W. H. Jo, supra; E. S. Lee et al., Poly(L-histidine)-PEG block copolymer micelles and pH-induced destabilization, 90 J. Control. Release 363-374 (2003)) and observed substantial nanogel volumetric expansion within cell endosomes, virogels are thought to be able to physically disrupt endosomal membranes. This endosomal disruption allows the virogels and DOX (released from the virogels) to transfer from the endosomes to the cytosol wherein the virogels rapidly shrink back to their original size under the new, more neutral local pH, and thereby reduce the DOX release rate. Free DOX, released under endosomal pH stimulus and now in the cytosol, then diffuses into the nucleus, the pharmacological target site. DOX action on the cells induces apoptosis, and eventually cell lysis, S. Wang et al., Doxorubicin induces apoptosis in normal and tumor cells via distinctly different mechanisms. Intermediacy of H$_2$O$_2$- and p53-dependent pathways, 279 J. Biol. Chem. 25535-25543 (2004). Cell lysis then releases the virogels from the cell for subsequent infection and action in neighboring cells.

Example 7

A2780/AD cells (obtained from J. Kopecek, University of Utah, Salt Lake City, Utah) were treated in culture medium with virogels (containing DOX 10 µg/ml equivalent) for 4 hours and in fresh medium (no virogel) for 20 hours. After 24 hours, culture medium (pH 7.4) was extracted and dropped to the AFM shell (ThermoMicroscopes Explorer with ECU-Plus Electronics) for investigation. For evaluating images of virogels collected from culture medium, virogels (0.01 wt %) suspended in fresh PBS pH 7.4 solution (ionic strength: 0.15) was also visualized.

Figure 6:
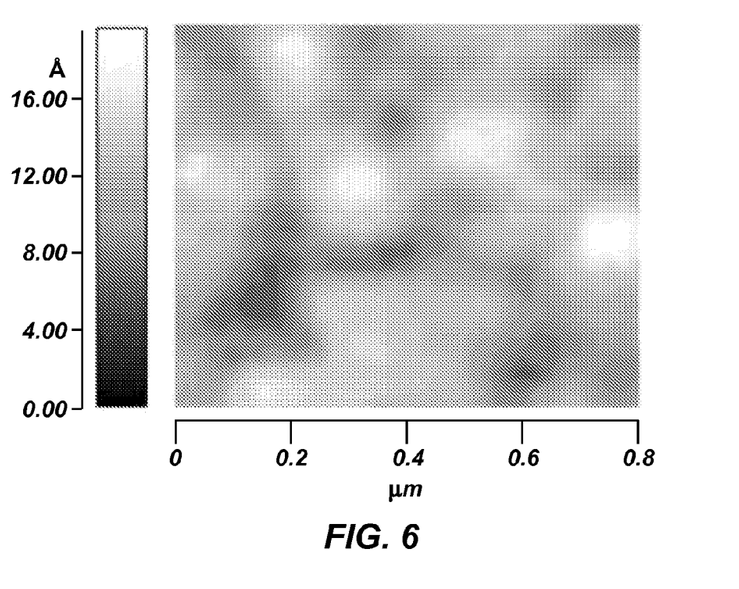
FIG. 6 shows an atomic force microscopy (AFM) image of DOX-loaded virogels released from lysed DOX-resistant A2780/AD cells and collected from culture medium (pH 7.4).

FIG. 6 shows an AFM image of DOX-loaded virogel particles in cell culture medium once freed from multi-drug resistant (MDR) ovarian cells (A2780/AD host cells), M. Tijerina et al., supra, after spontaneous cell lysis. Due to cell debris, the image was not as sharp as ordinary well-prepared simpler biological samples. However, the images clearly show that virogels were present in the same medium that contained no virogels when the medium was replaced prior to spontaneous cell lysis.

Example 8

Experiments were conducted to verify migration of virogels to neighboring cells. Cells grown on glass slide fragments ("plates") (1×1 cm) were pre-treated with free DOX (10 µg/ml) or equivalent DOX-loaded virogels or NPs (controls), E. S. Lee, K. Na & Y. H. Bae, Polymeric micelle for tumor pH and folate-mediated targeting, 91 J. Control. Release 103-113 (2003)) for 4 hours. These pretreated cells (A cells) were washed with PBS (pH 7.4) and co-cultured with fresh cells (B-0 cells) on new glass slide fragments for 20 hours in fresh culture medium. Co-culturing was carried out by placing a plate containing A cells and a plate containing B-0 cells next to each other, but separated by 1 mm, in a culture dish such that the A cells and B-0 cells continuously shared fresh culture medium. The A cells served as a potential source for migration of virogels, and the B-0 cells were a potential site for secondary virogel infection.

After the B-0 cells were co-cultured with A cells for 20 hours, such B-0 cells were redesignated as B-1 cells. B-1 cells were then withdrawn from the culture dish and were co-cultured with fresh cells on new glass slide fragments for 20 hours in fresh culture medium. These fresh cells that had been co-cultured with B-1 cells were termed B-2 cells. These B-2 cells were then also withdrawn and co-cultured with fresh cells on new glass slide fragments for 20 hours in fresh culture medium. These fresh cells that had been co-cultured with B-2 cells were termed B-3 cells. Confocal slice images were obtained, as described above, for observing fluorescent DOX in cells. To evaluate the effect of DOX on virogel migration, blank virogels (50 µg/ml) were tested using the same procedure. FITC-labeling (Example 2) was used to visualize the blank virogels.

Figure 7:
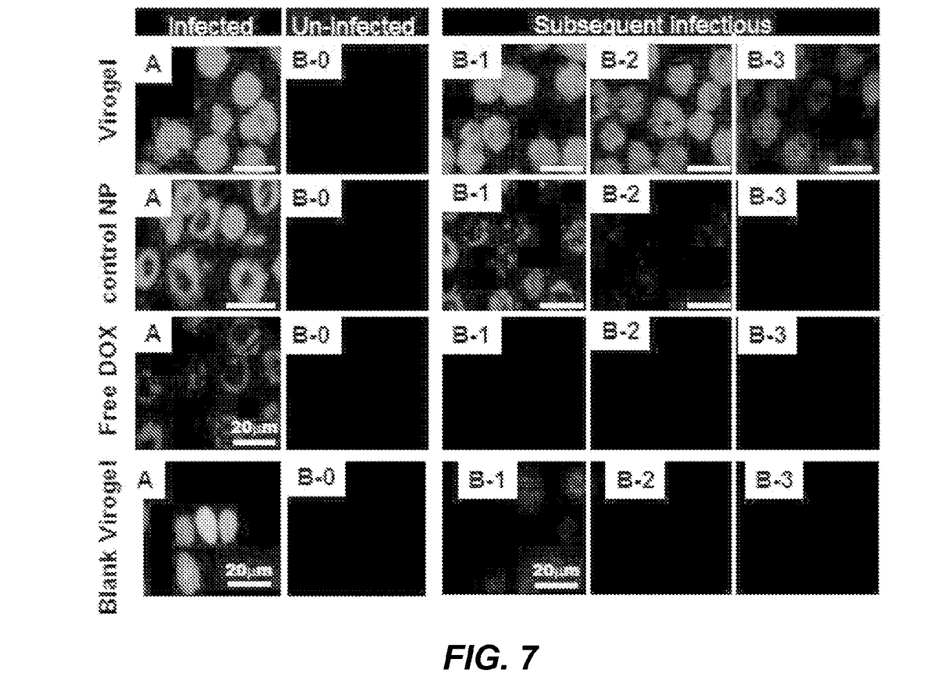
FIG. 7 shows migration of DOX-loaded virogels from infected A2780/AD cells to untreated cells, whereas control nanoparticles (NPs; about 70 nm in diameter), free DOX, and blank virogels showed no such migration.

The primary infected cell group (A cells) was observed using confocal microscopy, where cells appear red because of the intrinsic DOX fluorescence within the virogel (FIG. 7). DOX spread evenly within the cells, even in the nucleus, while the untreated cell group (B-0 cells) appeared dark, exhibiting no fluorescence. After co-incubation of the primary virogel "infected" cells (A cells) and untreated cells (B-0 cells) for 20 hours, the red DOX fluorescence appeared in the untreated cell group (B-1), even in the cell nucleus. This clearly demonstrates virogel migration from the pretreated cell group (A cells) to the co-cultured, untreated cell group (B-1 cells), suggesting secondary "infection." After being washed to remove free virogels in the culture medium, the glass plate with the second infected cell group (B-1 cells) was placed next to another uninfected, fresh cell group. The fresh group was spontaneously infected again after 20 hours (B-2). The DOX fluorescence intensity, however, diminished. The same procedure was repeated yet again, and another infection cycle occurred, but this time with a very weak DOX signal (B-3). The increasingly weakened "infection signal" (i.e., fluorescence) over repeated cycles is probably due to the loss of virogels by medium replacement, DOX depletion from the virogels, and reduced release of DOX during each cell cycle, eventually falling below a drug concentration required to produce cell death.

Three control experiments support the repeated infection capabilities of virogels. First, nanoparticles (NPs), E. S. Lee, K. Na & Y. H. Bae, 91 J. Control. Release 103-113 (2003), comprising a pH-insensitive central core of poly(L-lactic acid) and DOX, with all remaining nanoparticle components identical to the virogel, exhibited different behavior in cells. The red fluorescence attributable to DOX was observed homogeneously everywhere but within the nucleus, indirectly indicating that, unlike virogels, these pH-insensitive NPs (controls) have no capability for endosomal escape, resulting in cytosolically trapped DOX. The control NPs were able to produce secondary infection very weakly in the first cycle after 20 hours, explained by active endosomal recycling in resistant cells, as previously described, G. Mohajer, E. S. Lee & Y. H. Bae, Enhanced intercellular retention activity of a novel pH-sensitive polymeric micelles in wild and multidrug resistant MCF-7 cells, Pharm. Res. (in press), rather than apoptotic cell death. Second, experiments with free DOX produced only limited fractions of DOX diffusing into cells in the primary infection cycle due to the drug-resistant, active P-glycoprotein DOX efflux pumps in A2780/AD cells. M. Tijerina et al., supra; G. Szakacs et al., supra. No further cell effects in subsequent cycles were observed, e.g., (B-1), (B-2), and (B-3). Third, virogels without DOX (blank virogels) were used to "infect" cells, and these blank virogels, when visualized by confocal microscopy, showed the BSA-FITC conjugate on the virogel outer layer as green fluorescence. After entry into the primary infected cells, the virogel green color was distributed evenly within the cells. Due to endosomal disruption attributed to virogel activity, the endosomal recycling activity was seriously dampened. G. Mohajer, E. S. Lee & Y. H. Bae, supra. No secondary infection was detected due to lack of cell death and lytic release of virogel particles.

Example 9

A2780 and A2780/AD cells suspended in RPMI 1640 medium (200 μl) were seeded in a 96-well plate and cultured for 24 hours before testing. Free DOX (5 μg/ml) or equivalent DOX-loaded samples (virogels and control NPs) were added to the medium-removed 96-well plate for cell cytotoxicity tests. The pH of the culture medium was adjusted to pH 7.4 or pH 6.8 for 48 hours during the test, as described in A. Patchornik et al., supra. Cell cytotoxicity was measured using the tetrazolium salt MTT assay. E. S. Lee, K. Na & Y. H. Bae, 5 Nano Lett. 325-329 (2005); E. S. Lee, K. Na & Y. H. Bae, 103 J. Control. Release 405-418 (2005).

Figure 8:
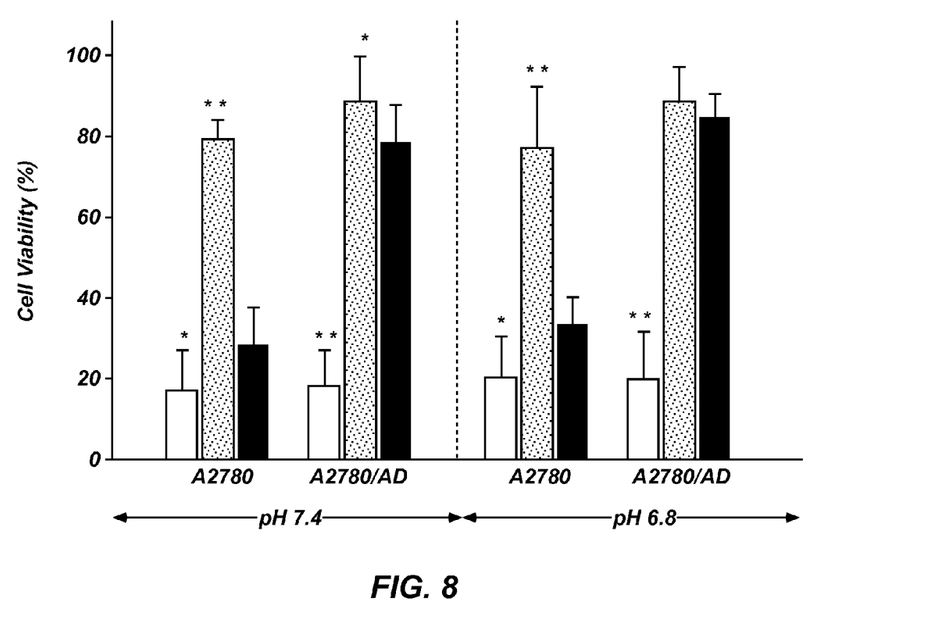
FIG. 8 shows viability of A2780 and drug-resistant A2780/AD tumor cells after treatment with DOX-loaded virogels (open bars), control NPs (shaded bars), or free DOX (dark bars) for 48 hours at pH 7.4 or pH 6.8. Each data point represents an average standard deviation (n=90) (*p<0.05, **p<0.01 for free DOX).

FIG. 8 shows impressive contrast for cytotoxicity at pH 7.4 for the various treatments. The viability of both drug-sensitive A2780 and drug-resistant analogues was below 20% when treated at a DOX equivalent concentration of 5 μg/ml carried by the virogels. However, DOX carried by the control NPs was not effective in killing cells. Free DOX at the same concentration showed a viability of 30% for sensitive cells, but of 80% for resistant cells. Similar results were obtained when these same experiments were conducted at pH 6.8, close to tumor extracellular pH. A. S. Ojugo et al., Measurement of the extracellular pH of solid tumors in mice by magnetic resonance spectroscopy: a comparison of exogenous (19)F and (31)P probes, 12 NMR Biomed. 495-504 (1999). These results suggest that DOX-loaded virogels are far more potent for sensitive cells than free DOX and do not distinguish sensitive and resistant cells in tumor cell killing capability.

The subject matter claimed is:

1. A drug delivery vehicle for targeted delivery of a drug to a selected site, the drug delivery vehicle comprising a hydrophobic polymeric core configured for receiving the drug, a hydrophilic inner shell coupled to the core, a hydrophilic outer shell coupled to the inner shell, and a ligand coupled to the outer shell, wherein the core comprises poly(L-histidine-co-phenylalanine) blocks each containing about 32 histidine residues and about 6 phenylalanine residues.

2. The drug delivery vehicle of claim 1 wherein the hydrophilic inner shell comprises polyethylene glycol.

3. The drug delivery vehicle of claim 2 wherein the hydrophilic outer shell comprises a protein.

4. The drug delivery vehicle of claim 3 wherein the protein comprises bovine serum albumin.

5. The drug delivery vehicle of claim 4 wherein the bovine serum albumin is coupled to more than one polyethylene glycol.

6. The drug delivery vehicle of claim 1 wherein the hydrophilic outer shell comprises a protein.

7. The drug delivery vehicle of claim 6 wherein the protein comprises bovine serum albumin.

8. The drug delivery vehicle of claim 1 wherein the ligand comprises vitamins, hormones, interleukins, growth factors, neurotransmitters, viral surface components, antibodies, antigen-binding proteins, carbohydrates, or lectins.

9. The drug delivery vehicle of claim 8 wherein the ligand comprises folic acid.

* * * * *